(12) United States Patent
Phan et al.

(10) Patent No.: US 6,904,303 B2
(45) Date of Patent: Jun. 7, 2005

(54) APPARATUS FOR MAPPING AND COAGULATING SOFT TISSUE IN OR AROUND BODY ORIFICES

(75) Inventors: Huy D. Phan, San Jose, CA (US); David K. Swanson, Mountain View, CA (US); Josef V. Koblish, Palo Alto, CA (US); Russell B. Thompson, Los Altos, CA (US); Thomas R. Jenkins, Oakland, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/317,613

(22) Filed: Dec. 11, 2002

(65) Prior Publication Data

US 2003/0130572 A1 Jul. 10, 2003

Related U.S. Application Data

(62) Division of application No. 09/447,182, filed on Nov. 22, 1999, now Pat. No. 6,529,756.

(51) Int. Cl.⁷ .......................... A61B 5/042; A61B 18/14
(52) U.S. Cl. .......................... 600/374; 600/381; 606/41; 606/49; 607/99; 607/105; 607/113
(58) Field of Search .................................. 600/374, 381; 606/41, 49; 607/99, 105, 113, 122

(56) References Cited

U.S. PATENT DOCUMENTS

| | | | |
|---|---|---|---|
| 1,207,479 A | 12/1916 | Bisgaard | |
| 4,033,331 A | 7/1977 | Guss et al. | |
| 4,181,131 A | 1/1980 | Ogiu | |
| 4,245,624 A | 1/1981 | Komiya | |
| 4,650,466 A | 3/1987 | Luther | |
| 4,706,671 A | 11/1987 | Weinrib | |
| 4,747,405 A | 5/1988 | Leckrone | |
| 4,753,223 A | 6/1988 | Bremer | |
| 4,823,812 A | 4/1989 | Eshel et al. | |
| 4,826,087 A | 5/1989 | Chinery | |
| 4,921,484 A | 5/1990 | Hillstead | |
| 5,041,085 A | 8/1991 | Osbourne | |
| 5,098,412 A | 3/1992 | Shiu | |
| 5,156,151 A | 10/1992 | Imran | |
| 5,228,442 A | 7/1993 | Imran | |
| 5,239,999 A | 8/1993 | Imran | |
| 5,263,493 A | 11/1993 | Avitall | |
| 5,273,535 A | 12/1993 | Edwards | |
| 5,279,299 A | 1/1994 | Imran | |
| 5,306,245 A | 4/1994 | Heavan | |
| 5,327,885 A | 7/1994 | Griffith | |
| 5,368,567 A | 11/1994 | Lee | |

(Continued)

FOREIGN PATENT DOCUMENTS

| | | |
|---|---|---|
| DE | 3920707 A1 | 1/1991 |
| EP | 0238106 A1 | 9/1987 |
| EP | 0737487 A2 | 10/1996 |
| EP | 0868922 A2 | 10/1998 |
| EP | 0916360 A2 | 5/1999 |
| EP | 1042990 A1 | 10/2000 |
| WO | WO-95/10322 A1 | 4/1995 |
| WO | WO-96/00042 A1 | 1/1996 |
| WO | WO-97/17892 A1 | 5/1997 |
| WO | WO-97/37607 A2 | 10/1997 |
| WO | WO-97/42966 A1 | 11/1997 |
| WO | WO-98/26724 A1 | 6/1998 |
| WO | WO-99/02096 A1 | 1/1999 |
| WO | WO-99/34741 A1 | 7/1999 |
| WO | WO-00/01313 A1 | 1/2000 |

Primary Examiner—Lee S. Cohen
(74) Attorney, Agent, or Firm—Henricks, Slavin & Holmes LLP

(57) ABSTRACT

A probe that may be used to create circumferential lesions in body tissue and, in some implementations, may also be used to perform mapping functions. The probe includes a collapsible/expandable structure that supports electrodes or other operative elements against the body tissue.

23 Claims, 12 Drawing Sheets

U.S. PATENT DOCUMENTS

| | | |
|---|---|---|
| 5,368,592 A | 11/1994 | Stern |
| 5,370,675 A | 12/1994 | Edwards |
| 5,399,165 A | 3/1995 | Paul, Jr. |
| 5,415,656 A | 5/1995 | Tihon et al. |
| 5,437,665 A | 8/1995 | Munro |
| 5,439,006 A | 8/1995 | Brennen |
| 5,456,667 A | 10/1995 | Ham |
| 5,482,037 A | 1/1996 | Borghi |
| 5,487,385 A | 1/1996 | Avitall |
| 5,487,757 A | 1/1996 | Truckai |
| 5,500,012 A | 3/1996 | Brucker |
| 5,549,661 A | 8/1996 | Kordis |
| 5,571,088 A | 11/1996 | Lennox |
| 5,582,609 A | 12/1996 | Swanson |
| 5,595,183 A | 1/1997 | Swanson |
| 5,637,090 A | 6/1997 | McGee |
| 5,672,174 A | 9/1997 | Gough |
| 5,702,365 A | 12/1997 | King |
| 5,702,368 A | 12/1997 | Stevens |
| 5,702,438 A | 12/1997 | Avitall |
| 5,709,224 A | 1/1998 | Behl |
| 5,716,325 A | 2/1998 | Bonutti |
| 5,722,401 A | 3/1998 | Pietroski |
| 5,730,127 A | 3/1998 | Avitall |
| 5,738,683 A | 4/1998 | Osypka |
| 5,782,239 A | 7/1998 | Webster |
| 5,782,899 A | 7/1998 | Imran |
| 5,800,482 A | 9/1998 | Pomeranz |
| 5,800,484 A | 9/1998 | Gough |
| 5,820,591 A | 10/1998 | Thompson |
| 5,830,213 A | 11/1998 | Panescu |
| 5,836,947 A | 11/1998 | Fleischman |
| 5,860,974 A | 1/1999 | Abele |
| 5,863,291 A | 1/1999 | Schaer |
| 5,865,800 A | 2/1999 | Mirarchi |
| 5,879,295 A | 3/1999 | Li |
| 5,895,417 A | 4/1999 | Pomeranz |
| 5,910,129 A | 6/1999 | Koblish |
| 5,931,811 A | 8/1999 | Haissaguerre |
| 5,938,660 A | 8/1999 | Swartz |
| 5,971,983 A | 10/1999 | Lesh |
| 5,972,019 A | 10/1999 | Engelson |
| 6,012,457 A | 1/2000 | Lesh |
| 6,013,052 A | 1/2000 | Durman |
| 6,016,811 A | 1/2000 | Knopp |
| 6,024,740 A | 2/2000 | Lesh |
| 6,027,473 A | 2/2000 | Ponzi |
| 6,029,671 A | 2/2000 | Stevens |
| 6,048,329 A | 4/2000 | Thompson |
| 6,064,902 A | 5/2000 | Haissaguerre |
| 6,071,274 A | 6/2000 | Thompson |
| 6,071,279 A | 6/2000 | Whayne |
| 6,071,281 A | 6/2000 | Burnside |
| 6,086,581 A | 7/2000 | Reynolds |
| 6,117,101 A | 9/2000 | Diederich |
| 6,117,154 A | 9/2000 | Barbut |
| 6,120,500 A | 9/2000 | Bednarek |
| 6,152,899 A | 11/2000 | Farley |
| 6,161,543 A | 12/2000 | Cox |
| 6,164,283 A | 12/2000 | Lesh |
| 6,179,835 B1 | 1/2001 | Panescu |
| 6,190,382 B1 | 2/2001 | Ormsby |
| 6,203,525 B1 | 3/2001 | Whayne |
| 6,214,002 B1 | 4/2001 | Fleischman |
| 6,251,093 B1 | 6/2001 | Valley |
| 6,306,133 B1 | 10/2001 | Tu et al. |
| 6,325,797 B1 | 12/2001 | Stewart |
| 6,402,746 B1 | 6/2002 | Whayne |
| 6,413,234 B1 | 7/2002 | Thompson |
| 6,454,758 B1 | 9/2002 | Thompson |
| 6,464,700 B1 | 10/2002 | Koblish |
| 6,485,489 B2 | 11/2002 | Teirstein et al. |
| 6,529,756 B1 | 3/2003 | Phan |
| 6,542,781 B1 | 4/2003 | Koblish |
| 6,607,505 B1 | 8/2003 | Thompson |
| 6,613,046 B1 | 9/2003 | Jenkins |
| 6,645,199 B1 | 11/2003 | Jenkins |
| 2001/0007070 A1 | 7/2001 | Stewart |
| 2003/0069570 A1 | 4/2003 | Witzel et al. |

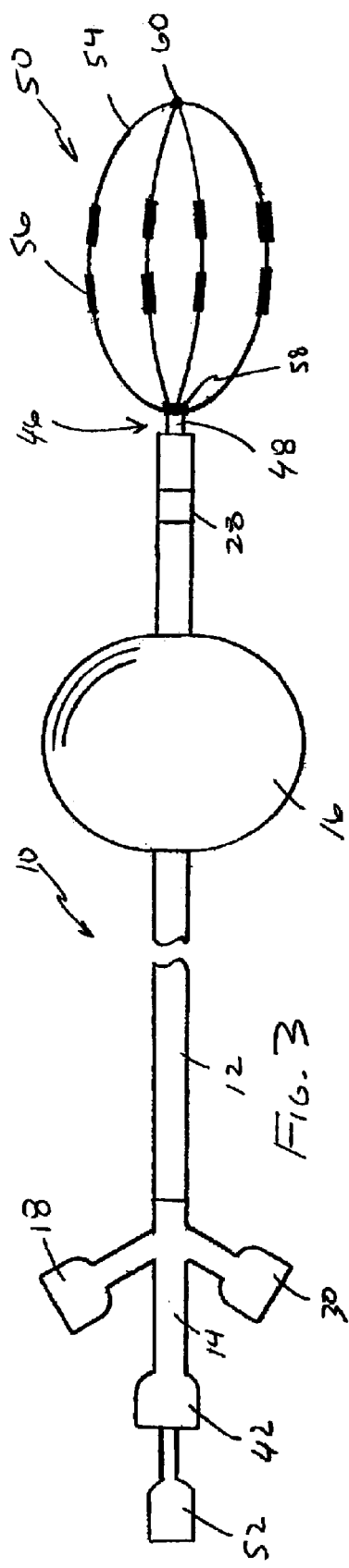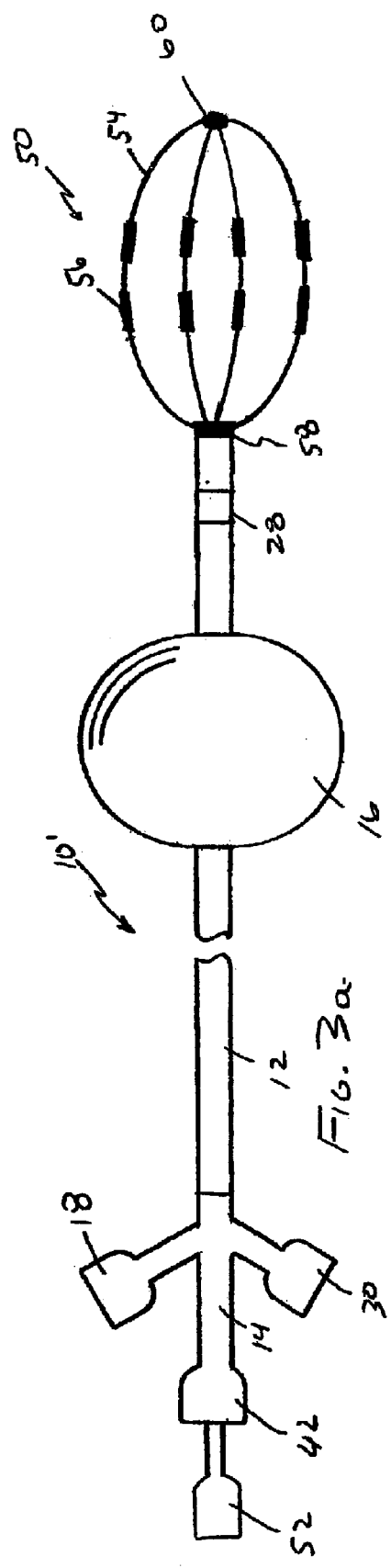

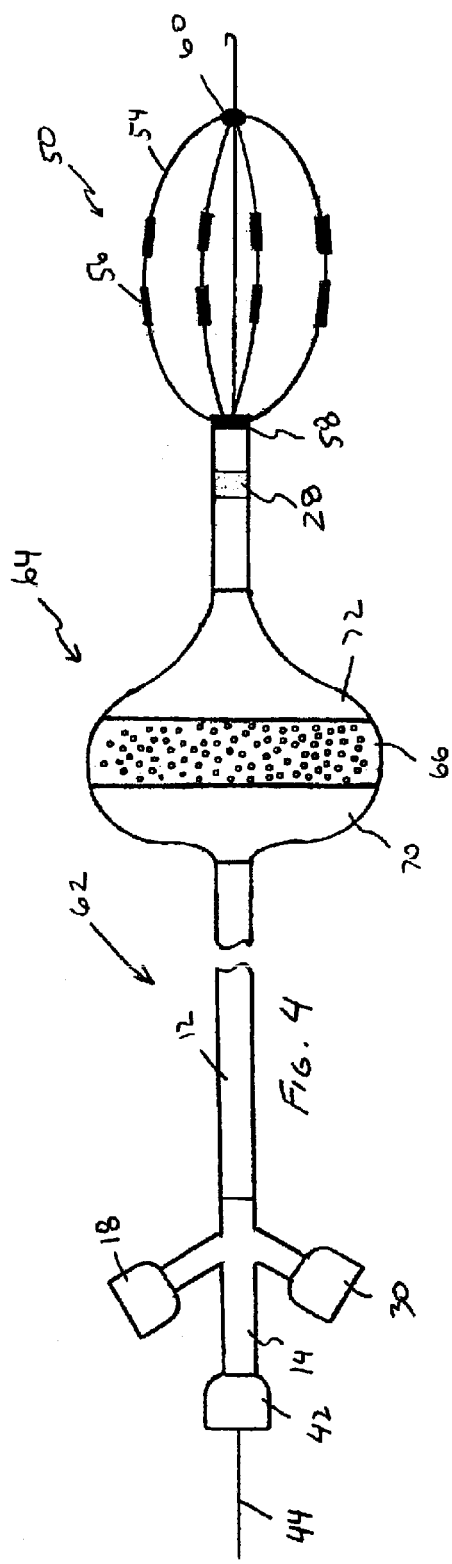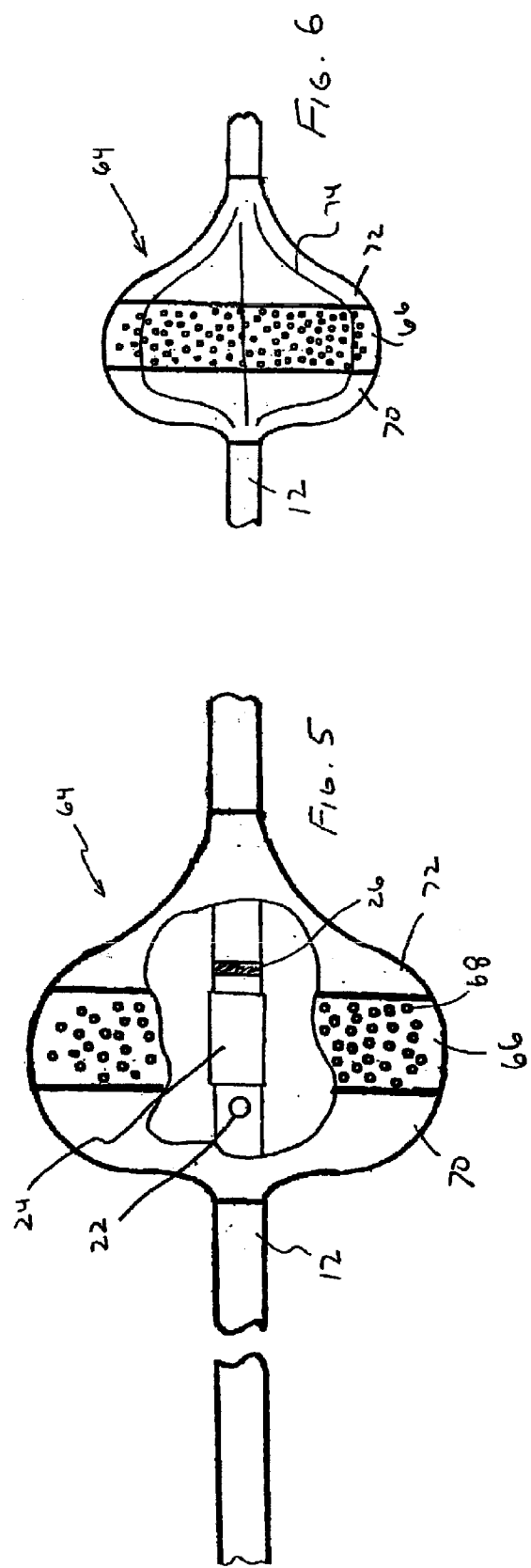

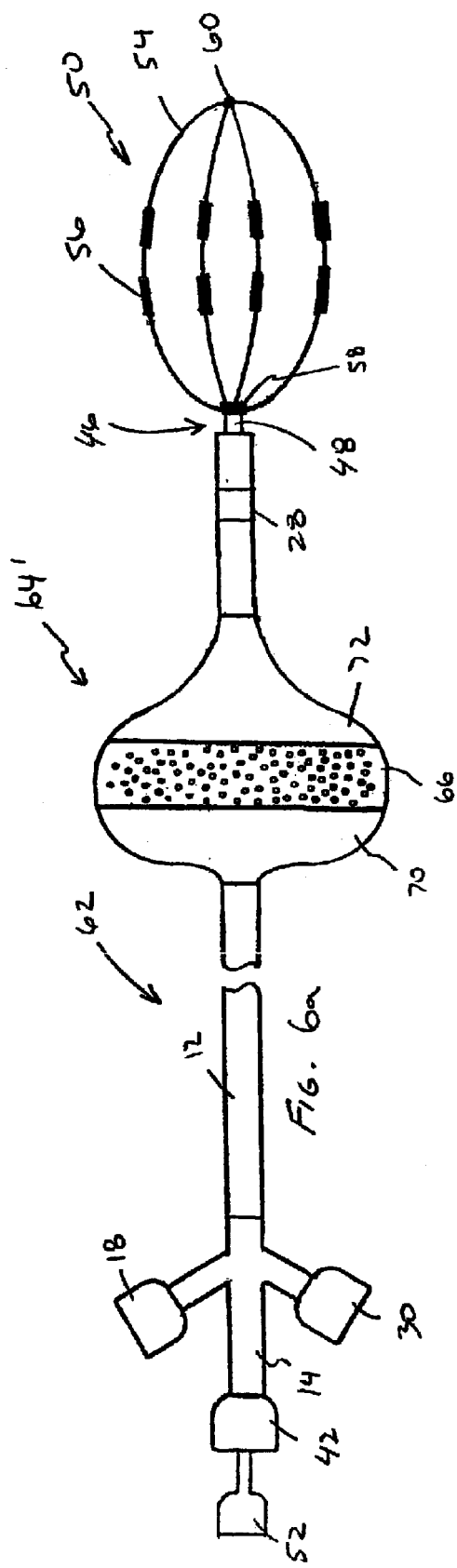

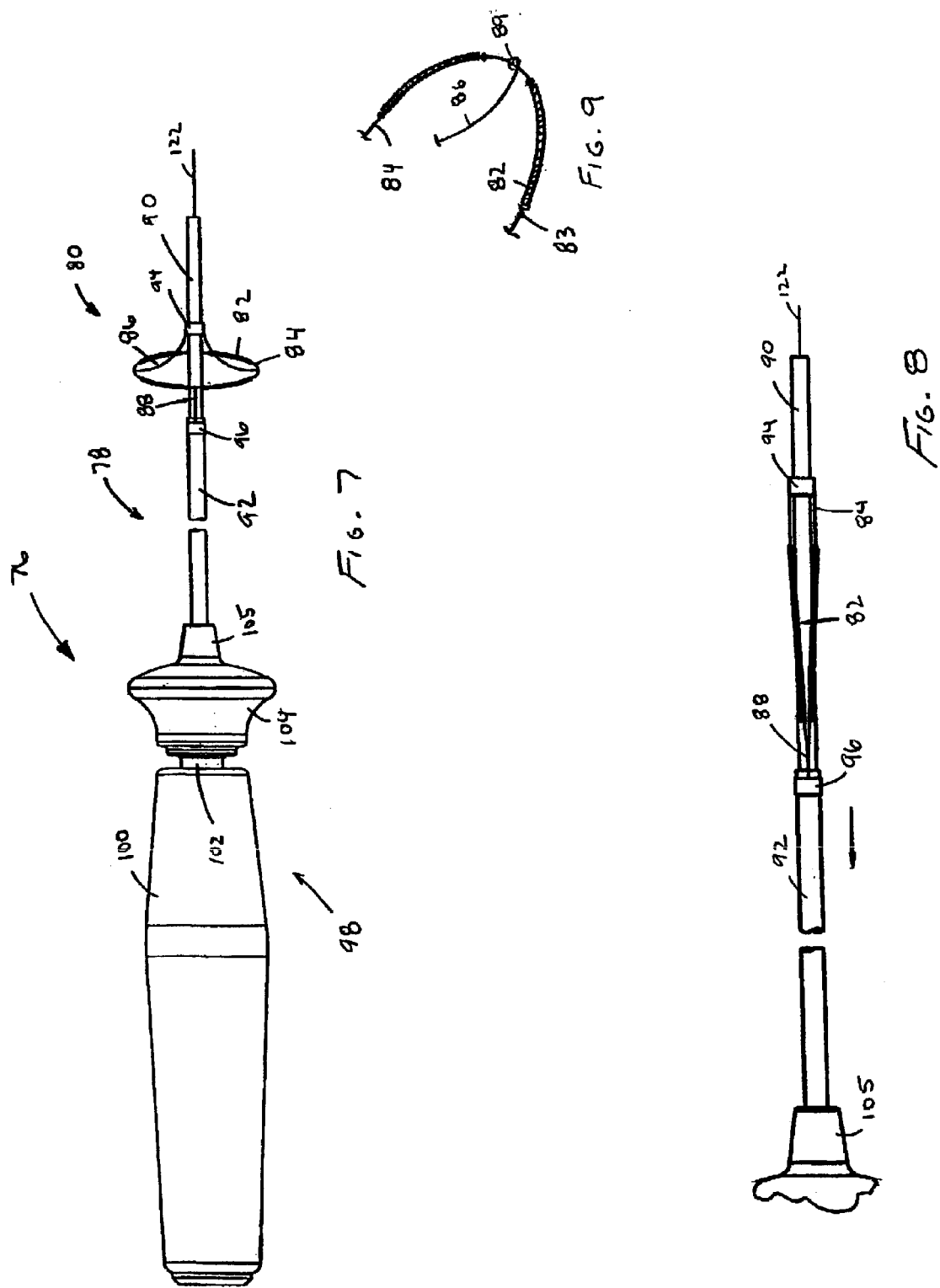

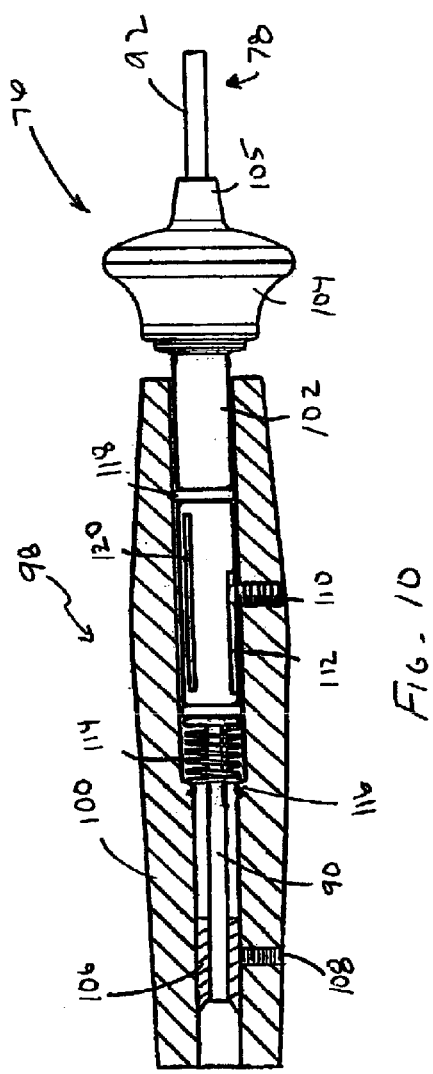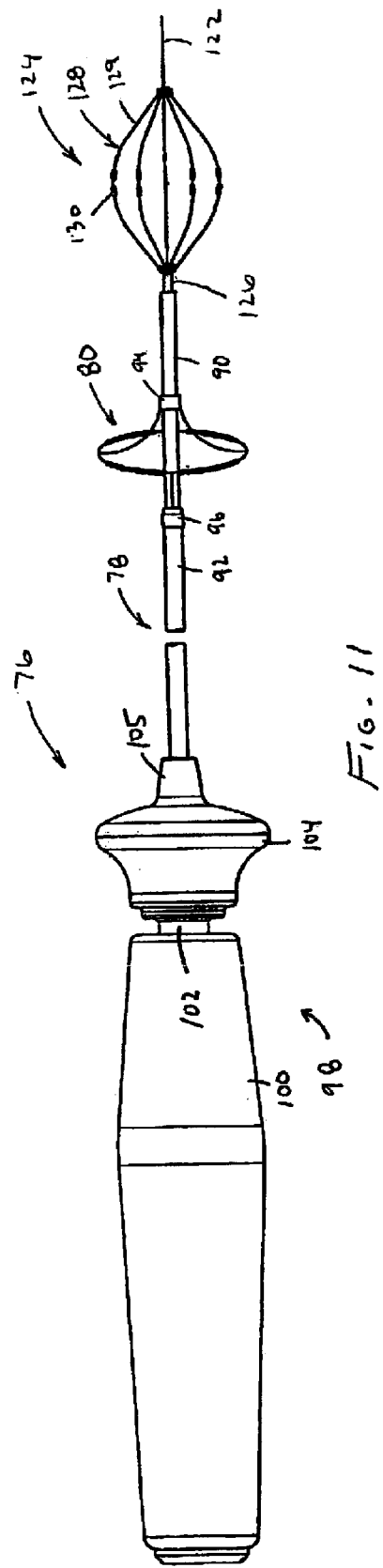

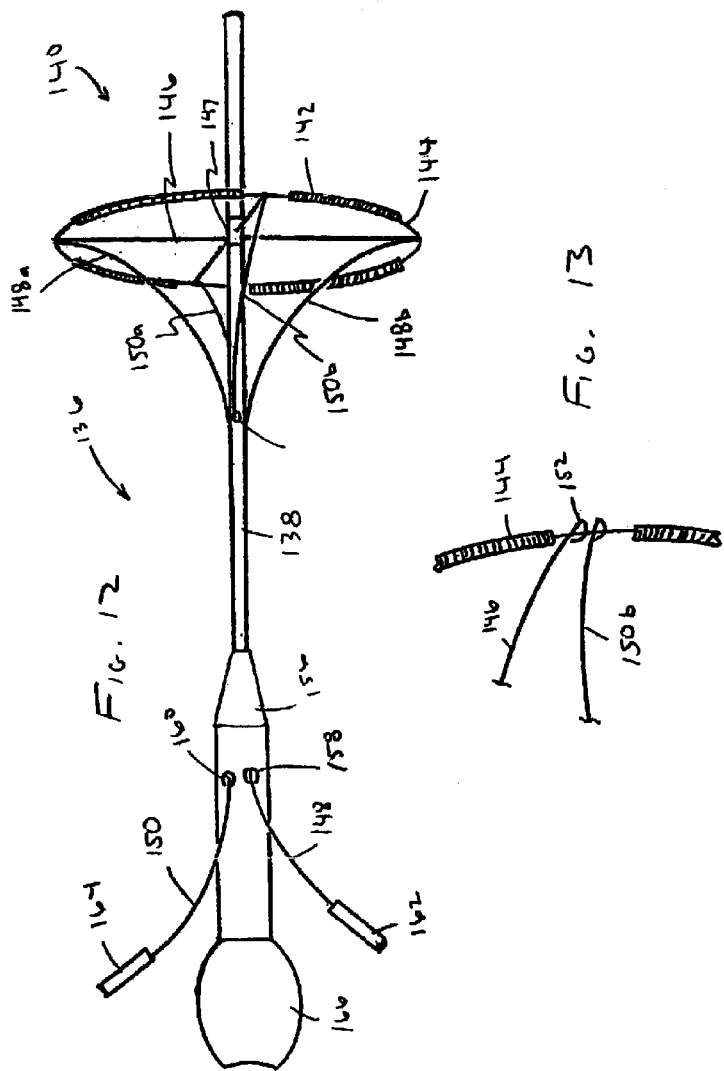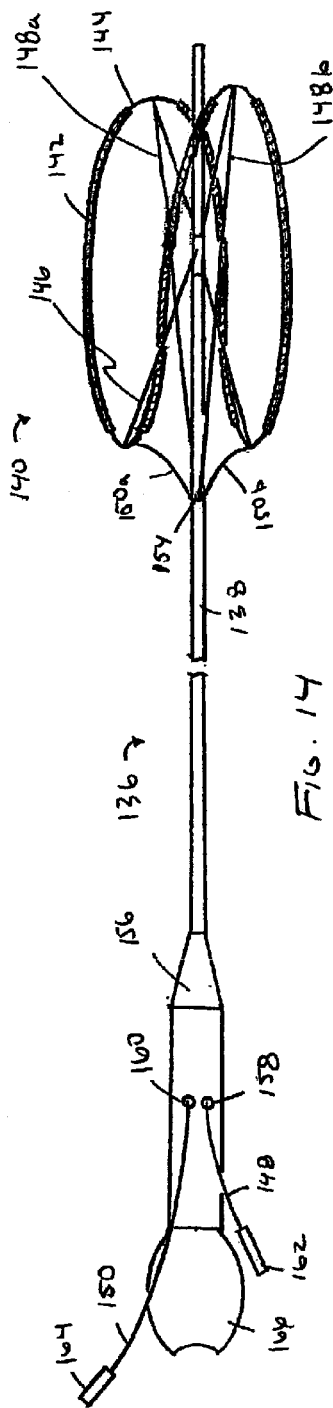

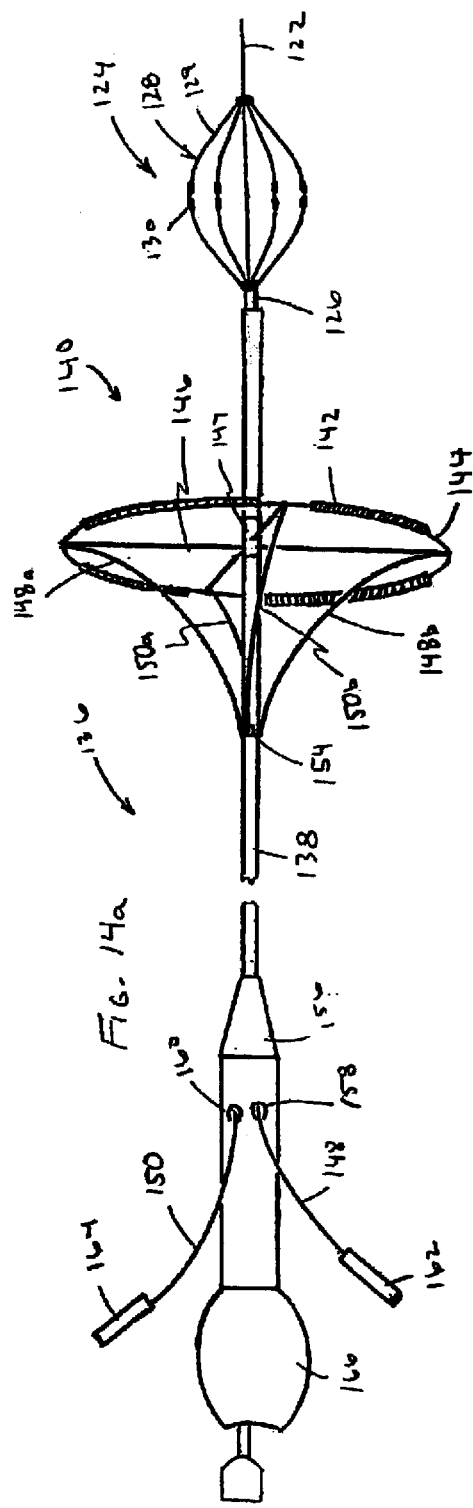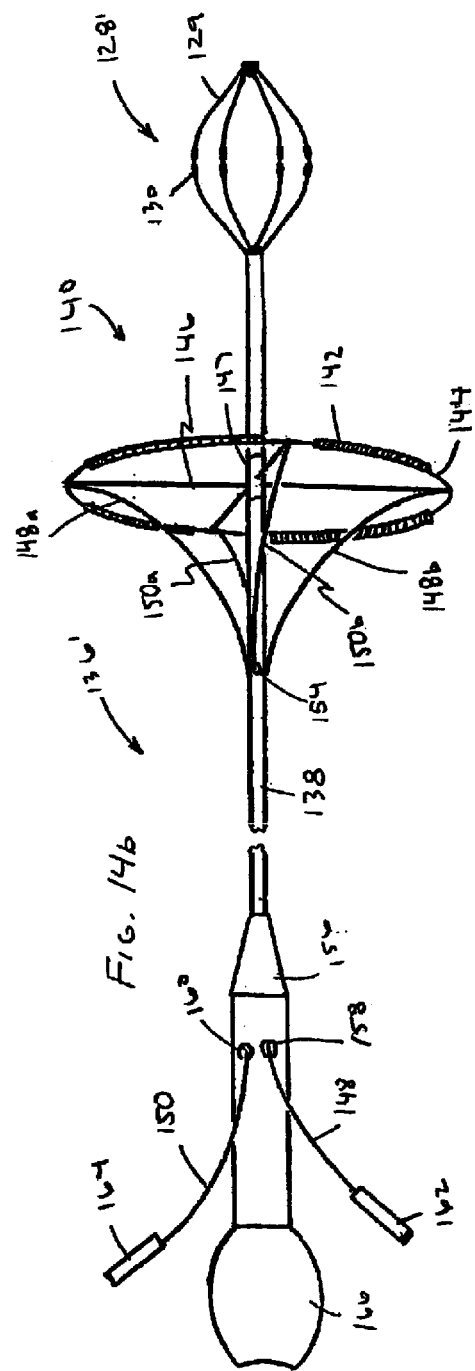

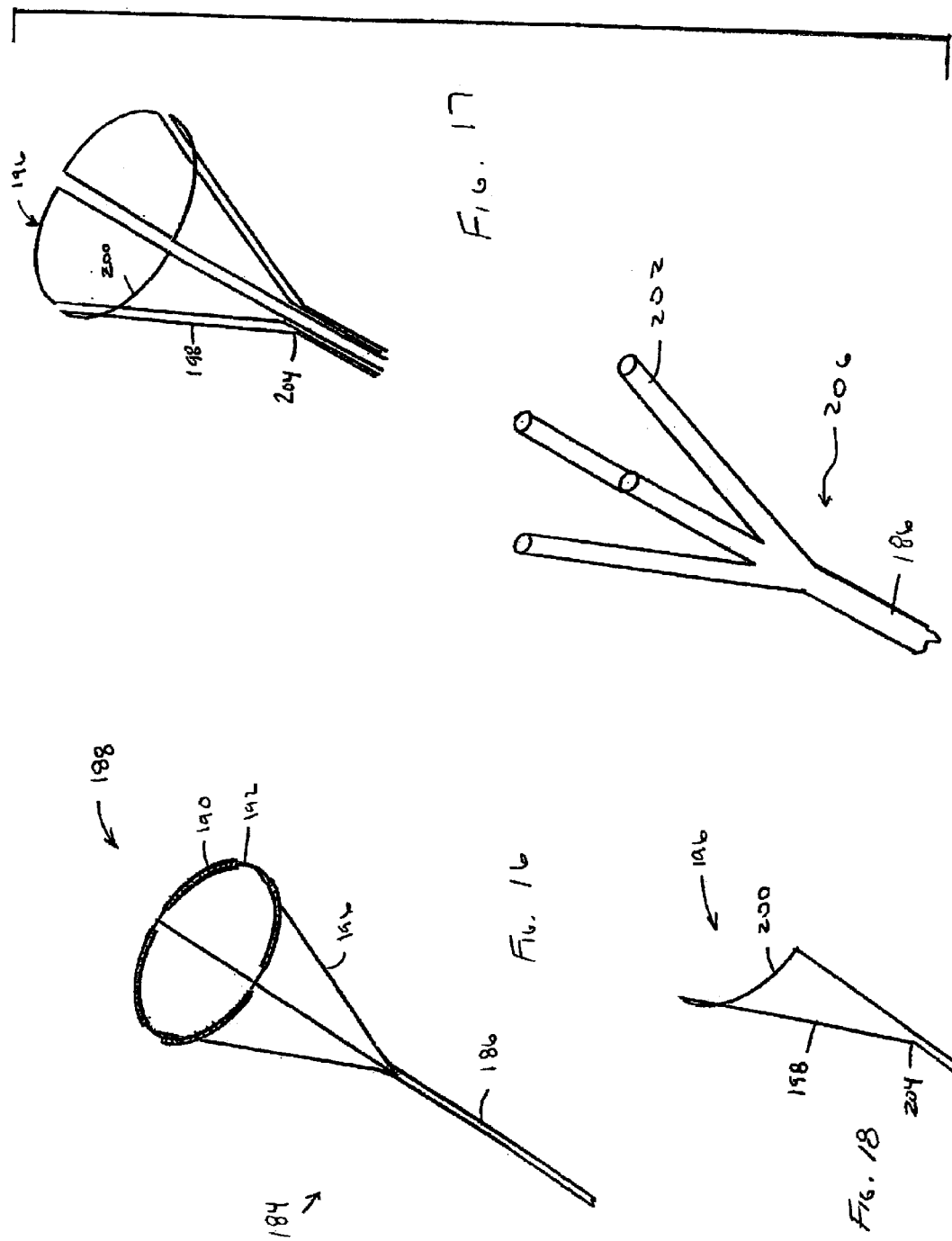

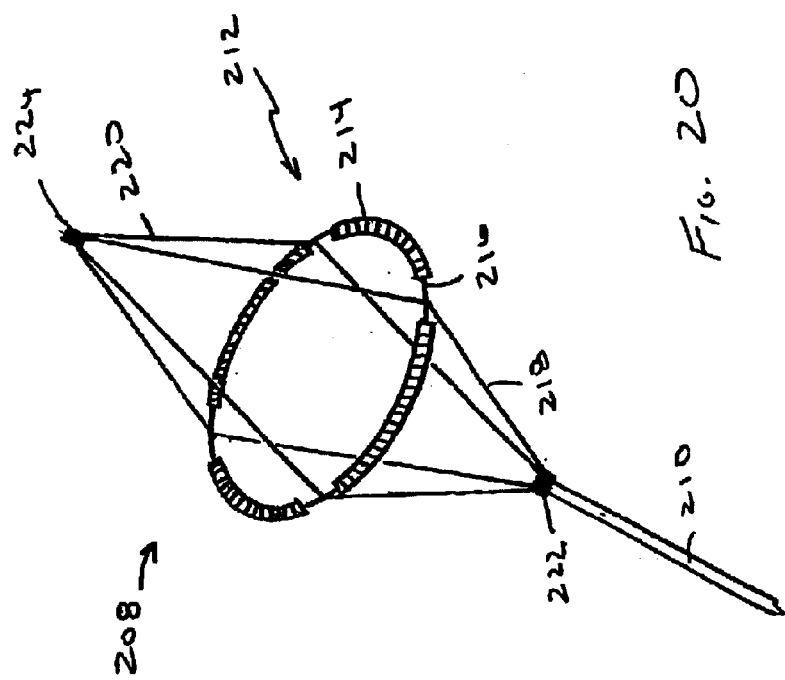
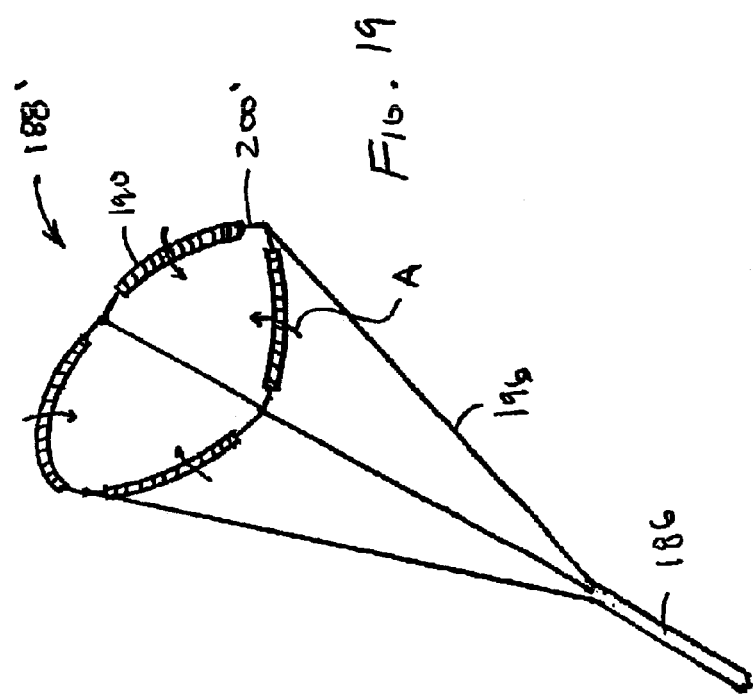

APPARATUS FOR MAPPING AND COAGULATING SOFT TISSUE IN OR AROUND BODY ORIFICES

This application is a divisional of U.S. application Ser. No. 09/447,182, filed Nov. 22, 1999, now U.S. Pat. No. 6,529,756.

BACKGROUND OF THE INVENTIONS

1. Field of Inventions

The present inventions relate generally to medical devices that support one or more diagnostic or therapeutic elements in contact with body tissue and, more particularly, to medical devices that support one or more diagnostic or therapeutic elements in contact with bodily orifices or the tissue surrounding such orifices.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in co-pending U.S. application Ser. No. 08/769,856, filed Dec. 19, 1996, and entitled "Loop Structures for Supporting Multiple Electrode Elements." The loop is formed as the catheter is pushed in the distal direction. The loop may also be formed by securing a pull wire to the distal end of the catheter that extends back through the sheath, as is illustrated in U.S. Pat. No. 5,910,129, which is incorporated herein by reference. Loop catheters are advantageous in that they tend to conform to different tissue contours and geometries and provide intimate contact between the spaced tissue coagulation electrodes (or other diagnostic or therapeutic elements) and the tissue.

Mapping baskets, which may be carried on the distal end of separate mapping catheters, are often used to locate the reentry pathways prior to the formation of lesions. Exemplary mapping baskets are disclosed in U.S. Pat. No. 5,823,189. Additionally, once the lesions have been formed, the mapping baskets are again used to determine whether the lesions have successfully eliminated the reentry pathways. Mapping baskets are superior to conventional diagnostic catheters because mapping baskets do not need to be steered to a variety of sites within a bodily region such as the pulmonary vein during a diagnostic procedure and, instead, can perform a diagnostic procedure in a single beat from a single location.

The use of a mapping catheter in combination with a soft tissue coagulation catheter can, however, be problematic. For example, when a mapping catheter is used in combination a soft tissue coagulation catheter, a pair of transseptal punctures (or a single relatively large puncture) must be formed in the atrial septum so that the catheters can be advanced from the right atria, through the fossa ovalis and into the left atria. Two punctures (or a relatively large single puncture) must also be formed in the femoral vein. In addition, the time required to manipulate two catheters into their respective positions can lead to prolonged periods of fluoroscopy.

The issues associated with the combined use of mapping and coagulation catheters notwithstanding, one lesion that has proven to be difficult to form with conventional catheters is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. Conventional steerable catheters and loop catheters have proven to be less than effective with respect to the formation of such circumferential lesions. Specifically, it is difficult to form an effective circumferential lesion by forming a pattern of relatively small diameter lesions.

Accordingly, the inventors herein have determined that a need exists for a device that is capable of both mapping and coagulating tissue. The inventors herein have further determined that a need exists generally for structures that can be used to create circumferential lesions within or around bodily orifices. The inventors herein have also determined that a need exists for a device that can both map the pulmonary vein and create lesions within or around the pulmonary vein.

SUMMARY OF THE INVENTION

Accordingly, the general object of the present inventions is to provide a device that avoids, for practical purposes, the aforementioned problems. In particular, one object of the present inventions is to provide a device that can be used to create circumferential lesions in or around the pulmonary vein and other bodily orifices in a more efficient manner than conventional apparatus. Another object of the present invention is to provide a device that can be used to both map the pulmonary vein and create lesions within or around the pulmonary vein.

In order to accomplish some of these and other objectives, a probe in accordance with one embodiment of a present invention includes a support body, an expandable/collapsible tissue coagulation structure supported on the support body, and a mapping structure. The mapping structure may be supported on the support body distally of the expandable/collapsible tissue coagulation structure or, alternatively, passable through a lumen in the support body so that it can be advanced beyond the distal end of the support body. Such a probe provides a number of advantages over conventional apparatus. For example, the combination of the tissue coagulation structure and the mapping structure allows the physician to perform a mapping and coagulation procedure with a single instrument, thereby eliminating the aforementioned problems in the art. The mapping structure may also be positioned within the pulmonary vein or other orifice during a coagulation procedure and serve as an anchor to improve the accuracy of the placement of the coagulation structure. Additionally, the expandable tissue coagulation structure is especially useful for creating circular lesions in and around the pulmonary vein and other body orifices.

In order to accomplish some of these and other objectives, a probe in accordance with one embodiment of a present invention includes a support body defining a longitudinal axis, an expandable/collapsible hoop structure defining an open interior region and supported on the support body, at least one operative element supported on the expandable/collapsible hoop structure. Such a probe provides a number of advantages over conventional apparatus. For example, in an implementation where the operative element consists of a plurality of spaced electrodes, the hoop structure can be readily positioned such that the electrodes are brought into contact with tissue in or around the pulmonary vein or other bodily orifice. The hoop structure also defines an open region that allows blood or other bodily fluids to pass therethrough. As a result, the present probe facilitates the formation of a circumferential lesion without the difficulties associated with conventional apparatus and does so without the occlusion of blood or other fluids.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 3 is a side view of the probe illustrated in FIG. 1 in combination with a probe that supports a mapping basket.

FIG. 3a is a side view of a probe similar to the probe illustrated in FIG. 1 with an integral mapping basket.

FIG. 4 is a side view of a probe in accordance with a preferred embodiment of a present invention.

FIG. 5 is a cutaway view of a portion of the probe illustrated in FIG. 4.

FIG. 6 is a side view of a porous electrode illustrated in FIG. 4 with fold lines added thereto.

FIG. 6a is a side view of a probe similar to the probe illustrated in FIG. 4 with the mapping basket mounted on a separate probe.

FIG. 7 is a side view of a probe in accordance with a preferred embodiment of a present invention.

FIG. 8 is a partial side view of the probe illustrated in FIG. 7 in a collapsed orientation.

FIG. 9 is a partial perspective view of a portion of the probe illustrated in FIG. 7.

FIG. 10 is a side, partial section view of the probe handle illustrated in FIG. 7.

FIG. 11 is a side view of the probe illustrated in FIG. 7 in combination with a probe that supports a mapping basket.

FIG. 12 is a side view of a probe in accordance with a preferred embodiment of a present invention.

FIG. 13 is a partial perspective view of a portion of the probe illustrated in FIG. 12.

FIG. 14 is a side view of the probe illustrated in FIG. 12 in a collapsed orientation.

FIG. 14a is a side view of the probe illustrated in FIG. 12 in combination with a probe that supports a mapping basket.

FIG. 14b is a side view of a probe similar to the probe illustrated in FIG. 12 with an integral mapping basket.

FIG. 16 is a perspective view of a probe in accordance with a preferred embodiment of a present invention.

FIG. 17 is an exploded perspective view showing certain elements in the probe illustrated in FIG. 16.

FIG. 18 is perspective view of one of the structural members that forms the hoop structure illustrated in FIGS. 16 and 17.

FIG. 19 is a perspective view of a probe in accordance with a preferred embodiment of a present invention.

FIG. 20 is a perspective view of a probe in accordance with a preferred embodiment of a present invention.

DETAILED DESCRIPTION OF THE PREFERRED EMBODIMENTS

Figure 1:
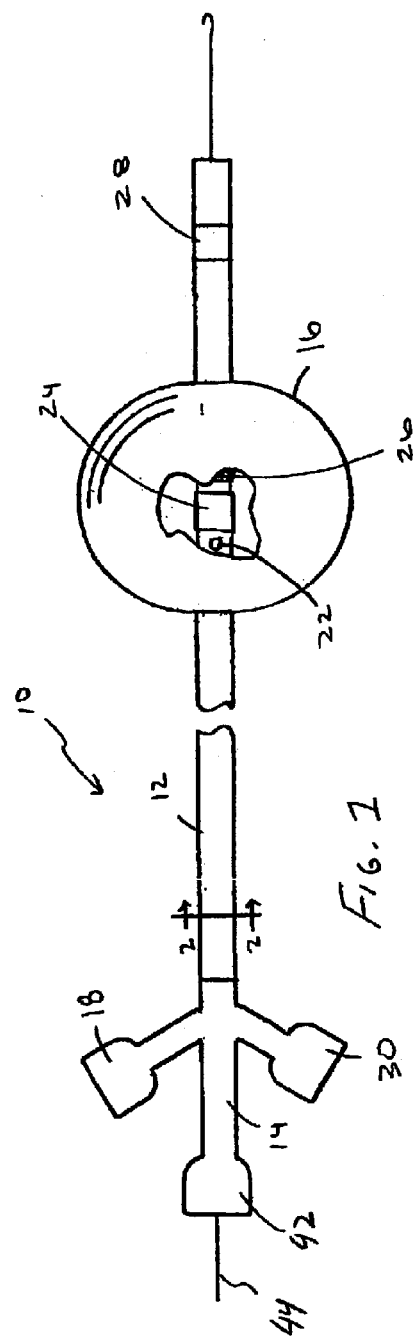
FIG. 1 is a side cutaway view of a probe in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Inflatable Structures
III. Hoop Structures
IV. Hoop Structure Electrodes, Temperature Sensing and Power Control The section titles and overall organization of the present detailed description are for the purpose of convenience only and are not intended to limit the present inventions.

I. Introduction

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, the distal portion of a catheter in accordance with a present invention, which may include diagnostic and/or soft tissue coagulation electrodes, can be used to create lesions within or around the pulmonary vein to treat ectopic atrial fibrillation.

The structures are also adaptable for use with probes other than catheter-based probes. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in co-pending U.S. application Ser. No. 09/072,872, filed May 5, 1998, and entitled "Surgical Methods and Apparatus for Positioning a Diagnostic or Therapeutic Element Within the Body."

Surgical probe devices in accordance with the present inventions preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

II. Inflatable Structures

Figure 2:
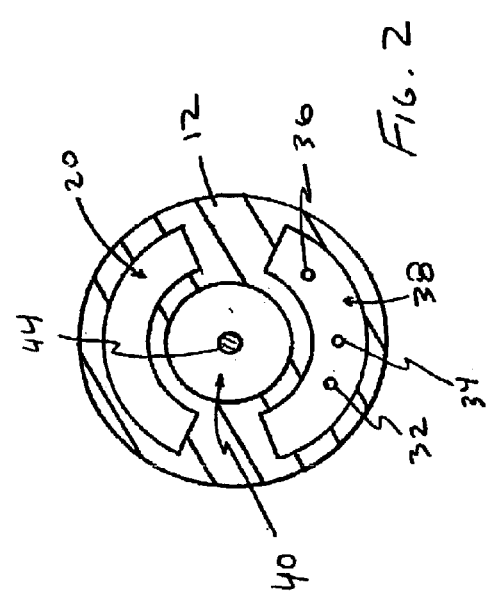
FIG. 2 is a section view taken along line 2—2 in FIG. 1.

As illustrated for example in FIGS. 1 and 2, a catheter 10 in accordance with a preferred embodiment of a present invention includes a flexible catheter body 12 that may be formed from a biocompatible thermoplastic material such as braided or unbraided Pebax® (polyether block emide), polyethylene, or polyurethane, and is preferably about 5 French to about 9 French in diameter. Preferably, the catheter body 12 will have a two part construction consisting of a relatively short flexible distal member (formed from unbraided Pebax®) and a longer less flexible proximal member (formed from braided Pebax®). The proximal and distal members may be bonded together with an overlapping thermal bond or adhesive bonded together end to end over a sleeve in what is referred to as a "butt bond." The proximal end of the catheter body 12 is secured to a handle 14. An expandable (and collapsible) coagulation body 16 is mounted near the distal end of the catheter body 12. As described below, the expandable coagulation body 16 may be heated to a temperature that will cause soft tissue in contact with the coagulation body to coagulate.

The expandable coagulation body 16, which is bonded to and disposed around the catheter body 12, can be inflated with water, hypertonic saline solution, or other biocompatible fluids. The fluid is supplied under pressure to the catheter 10 through an infusion/ventilation port 18. The pressurized fluid travels to and from the expandable coagulation body 16 through a fluid lumen 20 in the catheter body 12 and an aperture 22 located within the expandable coagulation body. Pressure is maintained to maintain the expandable coagulation body 16 in the expanded orientation illustrated in FIG. 1. The pressure should be relatively low (less than 5 psi) and will vary in accordance with the desired level of inflation, strength of materials used and the desired degree of body flexibility. The fluid may be removed from the expandable coagulation body 16 by applying a suction force to the infusion/ventilation port 18.

For applications associated with the creation of lesions in or around the pulmonary vein, the exemplary expandable coagulation body 16 is preferably located about 3 cm to about 5 cm from the distal tip of the catheter body 12 and the diameter is between about 2 mm and about 6 mm in the collapsed state and between about 10 mm and about 30 mm in the expanded (or inflated) state. Suitable materials for the expandable coagulation body 16 include relatively elastic thermally conductive biocompatible materials such as silicone and polyisoprene. Other less elastic materials, such as Nylon®, Pebax®, polyethylene and polyester, may also be used. Here, the expandable coagulation body will have to be formed with fold lines. [Note the discussion below concerning fold lines with respect to the exemplary embodiment illustrated in FIG. 6.] Additionally, although the exemplary expandable coagulation body 16 has a spherical shape, other shapes, such as a tear drop shape, a cylindrical shape, or a prolate ellipsoid, may also be employed.

A fluid heating element is located within the expandable coagulation body 16. In the preferred embodiment illustrated in FIGS. 1 and 2, the fluid heating element is an electrode 24 that is mounted on the catheter body 12. Alternatively, a bi-polar pair of electrodes may be used to transmit power through a conductive fluid, such as the aforementioned isotonic saline solution, to generate heat. The temperature of the fluid may be heated to about 90° C., thereby raising the temperature of the exterior of the expandable coagulation body 16 to approximately the same temperature for tissue coagulation. The electrode may be formed from metals such as platinum, gold and stainless steel.

The expandable coagulation body 16 tends to produce relatively superficial lesions. As such, it is especially useful for creating lesions within the pulmonary vein.

The temperature of the fluid is preferably monitored for power control purposes. To that end, a temperature sensing element, such as the illustrated thermocouple 26, may mounted on the catheter body 12 within the expandable coagulation body 16. A reference thermocouple 28 may be positioned near the distal end of the catheter body 12. Alternatively, a thermistor or other temperature sensing element may be used in place of the thermocouple and reference thermocouple arrangement. The electrode 24, thermocouple 26 and reference thermocouple 28 are respectively connected to an electrical connector 30 by electrical conductors 32, 34 and 36 which extend through a conductor lumen 38 in the catheter body. The connector 30 may be connected to a suitable RF power supply and control apparatus.

The exemplary catheter body 12 illustrated in FIGS. 1 and 2 also includes a central lumen 40 that is associated with a central port 42. The purpose of the central lumen is essentially two-fold. The central lumen 40 serves as a guidewire lumen when the probe 10 is being directed to a bodily region of interest such as the pulmonary vein. A guidewire 44 is first directed into the bodily region in conventional fashion and the probe 10 is then advanced over the guidewire. A relatively short introducer sheath may be used to facilitate insertion of the catheter 10 into the vasculature. Alternatively, a sheath which extends to the anatomical region of interest may be used. Once the probe reaches the bodily region of interest, the guidewire 44 may be removed so that the lumen can be used for its other purpose, which is to provide a passage to the bodily region for another device.

As illustrated for example in FIG. 3, a conventional basket catheter 46, such as the Constellation® basket catheter manufactured by EP Technologies, Inc. in San Jose, Calif., may be advanced through the central lumen 40. The exemplary basket catheter 46 includes an elongate catheter body 48, a mapping and/or coagulation basket 50 and a handle/electrical connector 52. The basket may include two to eight electrode supporting splines 54 and one to eight electrodes 56 on each spline. The splines 54, which are preferably made of a resilient, biologically inert material such as Nitinol® metal, stainless steel or silicone rubber, may be arranged either symmetrically or asymmetrically about the longitudinal axis of the basket 50. The splines 54 are connected between a base member 58 and an end cap 60 in a resilient, pretensed, radially expanded condition, to bend and conform to the endocardial tissue surface they contact.

The exemplary basket 50 illustrated in FIG. 3, which is intended to be inserted into the pulmonary vein for pacing and mapping thereof, includes four splines 54 that respectively support two electrodes 56. The basket 50 also has a substantially elliptical shape and is between about 20 mm and about 40 mm in diameter in its expanded state and about 5 cm in length. Additional details concerning basket structures are disclosed in U.S. Pat. No. 5,823,189, which is incorporated herein by reference.

The combination of the exemplary catheter 10 and basket catheter 46 allows the physician to perform mapping and coagulation procedure with a single instrument, thereby eliminating the aforementioned problems in the art. Moreover, the basket 50 may be positioned within the pulmonary vein or other orifice during a coagulation procedure and serve as an anchor to improve the accuracy of the placement of the expandable coagulation body 16. In those instances where the basket is not present, the distal portion of the catheter body can serve as the anchor.

Another exemplary catheter in accordance a present invention is illustrated in FIGS. 4–6 and generally represented by reference numeral 62. Catheter 62 is in many ways similar to the catheter illustrated in FIGS. 1–3 and like elements are represented with the like reference numerals. There are, however, two primary differences. Catheter 62 includes an expandable (and collapsible) porous electrode structure 64, as opposed to the heated expandable coagulation body 16, and the electrode supporting basket 50 is mounted on the distal portion of the catheter body 12, as opposed to being mounted on a separate catheter that is advanced through the central lumen 40.

As shown by way of example in FIG. 5, the expandable porous electrode 64, which is formed from an electrically non-conductive thermoplastic or elastomeric material, includes a porous region 66 having pores 68 and two non-porous regions 70 and 72. The pores 68, which are actually micropores, are shown diagrammatically in enlarged form for the purpose of illustration. Liquid pressure is used to inflate the expandable porous electrode 64 and maintain it in its expanded state. The liquid, which is supplied through the infusion/ventilation port 18 and fluid lumen 20 (FIG. 2), enters the expandable porous electrode 64 by way of the aperture 22. The expandable porous electrode 64 will then expand from its collapsed, low profile state (between about 2.3 mm and about 5.3 mm in diameter) to its expanded state (between about 10 mm and about 30 mm).

An electrode 24 formed from material with both relatively high electrical conductivity and relatively high thermal conductivity is carried within the expandable porous electrode 64. Suitable materials include gold, platinum, and platinum/iridium. Noble metals are preferred. Here too, the electrode 24, thermocouple 26 and reference thermocouple 28 are connected to the electrical connector 30 by electrical conductors 32, 34 and 36 which extend through conductor lumen 38 in the catheter body 12 (note FIG. 2). The liquid used to fill the expandable porous electrode 64 is an electrically conductive liquid that establishes an electrically conductive path to convey RF energy from the electrode 24 to tissue.

The pores 68 establish ionic transport of the tissue coagulating energy from the electrode 24 through the electrically conductive fluid to tissue outside the porous electrode 64. The liquid preferably possesses a low resistivity to decrease ohmic loses, and thus ohmic heating effects, within the porous electrode 64. The composition of the electrically conductive liquid can vary. A hypertonic saline solution, having a sodium chloride concentration at or near saturation, which is about 20% weight by volume is preferred. Hypertonic saline solution has a low resistivity of only about 5 ohm·cm, compared to blood resistivity of about 150 ohm·cm and myocardial tissue resistivity of about 500 ohm·cm.

Alternatively, the fluid can be a hypertonic potassium chloride solution. This medium, while promoting the desired ionic transfer, requires closer monitoring of the rate at which ionic transport occurs through the pores 68, to prevent potassium overload. When hypertonic potassium chloride solution is used, it is preferred keep the ionic transport rate below about 1 mEq/min.

Ionic contrast solution, which has an inherently low resistivity, can be mixed with the hypertonic sodium or potassium chloride solution. The mixture enables radiographic identification of the porous electrode 64 without diminishing the ionic transfer through the pores 68.

Due largely to mass concentration differentials across the pores 68, ions in the conductive fluid will pass into the pores because of concentration differential-driven diffusion. Ion diffusion through the pores 68 will continue as long as a concentration gradient is maintained across the porous electrode 64. The ions contained in the pores 68 provide the means to conduct current across the porous electrode 64. When RF energy is conveyed from a RF power supply and control apparatus to the electrode 24, electric current is carried by the ions within the pores 68. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of liquid through the pores 68. The ions convey RF energy through the pores 68 into tissue to a return electrode, which is typically an external patch electrode (forming a unipolar arrangement). Alternatively, the transmitted energy can pass through tissue to an adjacent electrode (forming a bipolar arrangement). The RF energy heats tissue (mostly ohmically) to coagulate the tissue and form a lesion.

The preferred geometry of the expandable porous electrode 64 is essentially tear drop-shaped and symmetric with a ring of pores 68 surrounded by non-porous regions. The ring is preferably about 2 mm to about 10 mm wide. This porous electrode configuration is especially useful for forming relatively deep lesions around the entrance to the pulmonary vein. However, nonsymmetrical or non tear drop-shaped geometries can be used. The porous electrode may, for example, be formed with a spherical shape. Elongated, cylindrical geometries can also be used. The distal non-porous region 72 may be eliminated and replaced with a porous region. The shape and size of the porous region 66 may also be varied.

With respect to materials, the porous region 66 of the expandable porous electrode 64 is preferably formed from regenerated cellulose or a microporous elastic polymer. Hydroscopic materials with micropores created through the use of lasers, electrostatic discharge, ion beam bombardment or other processes may also be used. The non-porous regions are preferably formed from relatively elastic materials such as silicone and polyisoprene. However, other less elastic materials, such as Nylon®, Pebax®, polyethylene, polyesterurethane and polyester, may also be used. Here, the expandable porous electrode 64 may be provided with creased regions 74 that facilitate the collapse of the porous electrode, as is illustrated for example in FIG. 6. A hydrophilic coating may be applied to the non-porous regions to facilitate movement of the porous electrode 64 in to and out of a sheath.

Like the exemplary catheter 10 illustrated in FIGS. 1–3, exemplary catheter 62 may be directed to the anatomical site of interest, such as the pulmonary vein, by advancing the catheter through a relatively short introducer sheath and over a guidewire 44. However, because the basket 50 is mounted on the distal end of the catheter, the base member 58 and end cap 60 are provided with apertures through which the guidewire 44 extends. A relatively short introducer sheath may be used to facilitate insertion of the catheter 62 into the vasculature or, alternatively, a sheath which extends to the anatomical region of interest may be used.

It should be noted that the exemplary catheter 10 illustrated in FIGS. 1–3 may be provided with a basket that is fixedly mounted on the distal end of the catheter body 12. Such a catheter is identified by reference numeral 10' in FIG. 3a. Similarly, the basket may be removed from the catheter 62 illustrated in FIGS. 4–6 so that a separate basket catheter may be used in combination therewith in a manner similar to that illustrated in FIG. 3. Such a catheter is identified by reference numeral 46' in FIG. 6a.

Additional information and examples of expandable and collapsible bodies are disclosed in U.S. patent application Ser. No. 08/984,414, entitled "Devices and Methods for Creating Lesions in Endocardial and Surrounding Tissue to Isolate Arrhythmia Substrates," U.S. Pat. Nos. 5,368,591, and 5,961,513, each of which is incorporated herein by reference.

III. Hoop Structures

As illustrated for example in FIGS. 7–10, a catheter 76 in accordance with an invention herein includes a catheter body 78 that supports a collapsible hoop structure 80 at or near its distal end. The hoop structure 80 may be used to support one or more operative elements in contact with an annular tissue region such as the pulmonary vein. For example, the hoop structure 80 may be used to support a plurality of spaced electrodes 82. The exemplary collapsible hoop structure 80 includes a substantially circular hoop spline 84, a pair of distal support splines 86 and a pair of proximal support splines 88. The shape of the hoop spline 84 may, alternatively, be oval, elliptical or any other two or three-dimensional shape required for a particular application. The end of each of the support splines 86 and 88 includes a loop 89 that encircles the corresponding portion of the hoop spline 84 in the manner illustrated in FIG. 9. Excessive movement of the support splines 86 and 88 around the circumference of the hoop spline 84 is prevented by the electrodes 82.

The exemplary collapsible hoop structure 80 may be driven from the expanded orientation illustrated in FIG. 7 to the collapsed orientation illustrated in FIG. 8 by moving the distal support splines 86 and proximal support splines 88 away from one another. In the illustrated embodiment, the catheter body 78 is configured to move the proximal and distal support splines 86 and 88 in this manner. More specifically, the catheter body 78 includes a pair of catheter body members 90 and 92 that are movable relative to one another. The catheter body members 90 and 92 are preferably tubular members arranged such that member 92 is slidably received within the lumen of member 90. The distal support splines 86 are secured to the catheter body member 90, while the proximal support splines 88 are secured to the catheter body member 92. When the catheter body member 92 is moved proximally relative to the catheter body member 90, the distal and proximal support splines 86 and 88 will be moved away from one another to collapse the hoop structure 80. Relative movement in the opposite direction will expand the support structure. Of course, the catheter body member 92 may be moved relative to the catheter body member 90, or both catheter body members may be moved, in other implementations of the invention.

In the exemplary embodiment illustrated in FIGS. 7–10, the distal and proximal support splines 86 and 88 are secured to the catheter body members 90 and 92 with anchor rings 94 and 96. The distal and proximal support splines 86 and 88 are preferably spot welded to the anchor rings 94 and 96 and the anchor rings are preferably glued to the catheter body members 90 and 92. Other methods of attachment may also be used.

The hoop spline 84, distal support splines 86 and proximal support splines 88 are preferably made of a resilient, biologically inert material such as Nitinol® metal, stainless steel or an elastic polymer (e.g. silicone rubber). The splines are preshaped into the configurations corresponding to an expanded hoop structure 80. In an implementation suitable for pulmonary vein applications, the hoop spline 84 will be about 10 mm to about 30 mm in diameter. The catheter body members 90 and 92 may be formed from a biocompatible thermoplastic material such as braided or unbraided Pebax®, polyethylene, or polyurethane. In an implementation suitable for pulmonary vein applications, the catheter body member 90 will have an outer diameter of about 1.5 mm and an inner diameter of about 1 mm, while the catheter body member 92 will have an outer diameter of about 2.2 mm and an inner diameter of about 1.6 mm.

The splines are preferably covered with tubes formed from a biocompatible polymer material such as Pebax® or Nylon®. Conductor wires (not shown) for the electrodes 82 and temperature sensors 83 (discussed in Section IV below) pass through the tubes and into the lumen of the catheter body member 90.

The exemplary catheter 76 also includes a handle 98 capable of moving the catheter body members 90 and 92 relative to one another. Referring more specifically to FIG. 10, the exemplary handle 98 includes a handle body 100 with a suitable electrical connector (not shown) for the conductor wires from the electrodes 82 and temperature sensors 83, a piston 102 that is slidably mounted in a longitudinally extending aperture in the handle body, and a thumb rest 104. The handle body 100, piston 102 and thumb rest 104 are preferably formed from machined or molded plastic. The catheter body member 92 is secured to a strain relief element 105 on the thumb rest 104 with an adhesive or other suitable instrumentality. The catheter body member 90 extends through the catheter body member 92, through a lumen formed in the piston 102 and into the proximal portion of the handle body 100. The catheter body member 90 is glued or otherwise secured to an anchor 106 which is itself held in place by a set screw 108 or other suitable device. As the position of the catheter body member 90 is fixed relative to the handle 100 and the piston 102 and proximal catheter body member 92 are not fixed relative to the handle, the catheter body member 92 may be moved relative to the catheter body member 90 by moving the piston.

In order to insure that the piston 102 in the exemplary handle 98 illustrated in FIGS. 7, 8 and 10 does not move once it has been placed in the position corresponding to a collapsed hoop structure 80, a set screw 110 engages a key way 112 formed in the piston. The friction force between the set screw 110 and key way 112 is sufficient to overcome the force generated by a collapsed hoop structure 80. Additionally, the longitudinal edges of the piston key way 112 limit the range of motion of the piston 102 by engaging the set screw 110. In the preferred embodiment, the length of the key way 112 is approximately 0.75 inch, but can range from approximately 0.375 inch to approximately 1.5 inches. Additionally, although the preferred embodiment includes the above-described set screw and key way arrangement, other mechanisms for applying a friction force to the piston and limiting its range of motion may also be employed. For example, fluting to limit the range of piston motion, a tapered collet, o-rings in addition to those discussed below, or a circumferential piston grip may be used in place of the preferred screw and key way arrangement.

The exemplary handle 98 also includes a compression spring 114 that applies a distally directed biasing force to the piston 102. The biasing force reduces the amount of force that must be applied to the piston 102 by the physician to move the piston in the distal direction and expand the hoop structure 80. The compression spring 114 is located between the proximal end of the piston 102 and an annularly shaped abutment 116. Because of the biasing force imparted to the piston 102 by the compression spring 114, the amount of physician-generated actuation force required to drive the piston is reduced.

A pair of o-rings 118 may be used to center the piston 102 within the handle body 100 of the exemplary handle 98. The o-rings 118 also prevent the piston from canting. The side of the exemplary piston 102 opposite the key way 112 includes a pair of Teflon® rods 120 which ride on the surface of the longitudinally extending aperture in the handle body 100. The Teflon® rods 120 provide improved lubricity and prevent the set screw 110 from driving the piston 102 into the surface of the aperture.

The exemplary catheter 76 may be advanced over a guidewire 122 (located within the inner lumen of the catheter body member 90) into the bodily region of interest in conventional fashion. A relatively short introducer sheath or a sheath which extends to the anatomical region of interest may be used if desired. The hoop structure 80 can then be expanded and used to create an annular lesion at the entrance to or within, for example, the pulmonary vein. Additionally, because the electrodes 82 or other operative elements are mounted on a hoop spline 84, tissue coagulation can be achieved without occluding blood flow.

The inner lumen of the catheter body member 90 may also be used to provide a passage to the bodily region for another device. As illustrated for example in FIG. 11, a conventional basket catheter 124, such as the Constellation® basket catheter manufactured by EP Technologies, Inc. in San Jose, Calif., may be advanced through the lumen of the distal catheter member 90. The basket catheter 124 may be advanced over the guidewire 122, as shown, or the guidewire may be removed from the lumen in the catheter body member prior to insertion of the basket catheter.

The exemplary basket catheter 124 includes an elongate catheter body 126, a mapping and/or coagulation basket 128 and a handle/electrical connector (not shown). Like the basket 50 described above with reference to FIG. 3, the exemplary basket 128 includes four symmetrically arranged splines 129, which are preferably made of a resilient, biologically inert material such as Nitinol® metal, stainless steel or silicone rubber. Each spline 129 supports two electrodes 130 and is supported in a resilient, pretensed, radially expanded condition between a base member 132 and an end cap 134. Basket catheter 124 is configured for use within the pulmonary vein and has a substantially elliptical shape and is between about 20 mm and about 40 mm in diameter in its expanded state and about 5 cm in length in the collapsed state. Nevertheless, the number of splines and electrodes on each spline, as well as the overall size of the basket 128, may be increased or decreased as applications require.

The combined catheter 76 and basket catheter 124 allows the physician to perform mapping and coagulation procedure with a single instrument, thereby eliminating the aforementioned problems in the art. The basket can also be used as an anchor to improve the accuracy of the placement of the hoop structure 80.

Figure 11A:
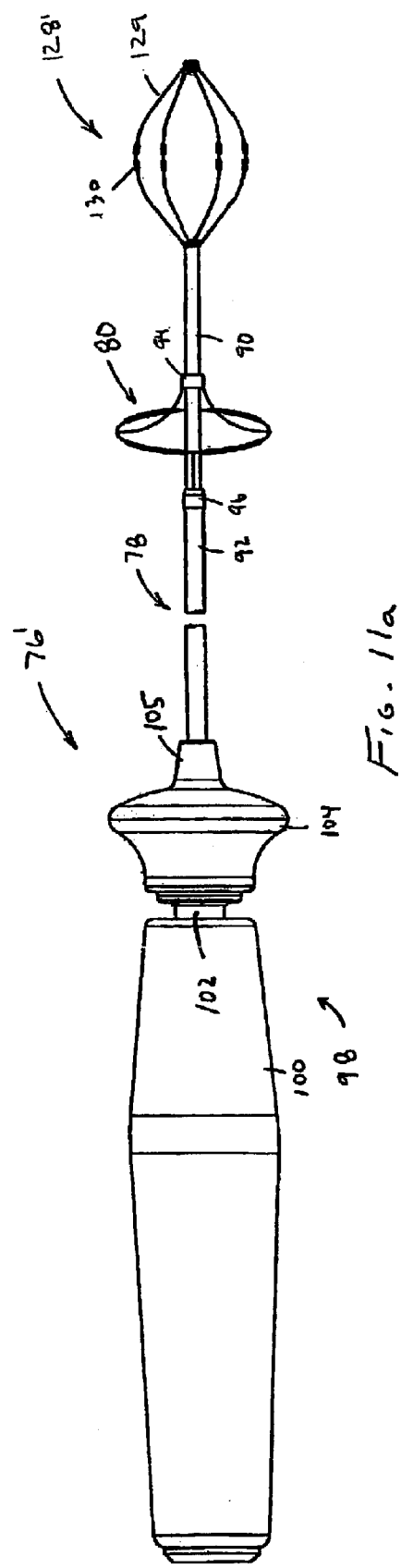
FIG. 11a is a side view of a probe similar to the probe illustrated in FIG. 7 with an integral mapping basket.

As illustrated for example in FIG. 11a, a catheter 76', which is otherwise identical to catheter 76, may include a basket 128' that is integral with distal end of the catheter body member 90. Here, the handle 100 would also include a suitable electrical connector for the basket 128'.

Another exemplary catheter including a collapsible hoop structure, which is generally represented by reference numeral 136, is illustrated in FIGS. 12–14. The catheter includes a catheter body 138 that supports a collapsible hoop structure 140. The hoop structure 140 may be used to support one or more operative elements in contact with an annular tissue region such as the pulmonary vein. For example, the hoop structure 140 may be used to support a plurality of spaced electrodes 142. The exemplary hoop structure 140 includes a substantially circular hoop spline 144 and four radially extending support splines 146. The shape of the hoop spline 144 may, alternatively, be oval, elliptical or any other shape required for a particular application. The support splines 146 are welded or otherwise secured to an anchor ring 147 that is mounted on the catheter body 138. The anchor ring 147 may be held in place with an interference fit, adhesive, or a combination thereof.

A first pair of stylets 148a and 148b and a second pair of stylets 150a and 150b are attached to the exemplary hoop spline 144. The ends support splines 146 and stylets 148a, 148b, 150a and 150b include respective loops 152 that encircle the corresponding portion of the hoop spline 144 in the manner illustrated in FIG. 13. The stylets 148a, 148b and 150a, 150b extend into a lumen within the catheter body 138 through apertures 154 and are wound into respective stylet pairs 148 and 150.

The catheter body 138 and support splines 146 may be formed from the same materials as their counterparts in the preferred embodiment illustrated in FIGS. 7–11. In particular, the support splines 146 are preferably formed from Nitinol® metal, stainless steel or an elastic polymer, and the anchor ring 147 should be formed from the same material as the support splines. The stylets 148a, 148b, 150a and 150b may be formed from inert wire such as Nitinol® or 17-7 stainless steel wire. The catheter body also includes lumens for the stylets, electrical conductors associated with the electrodes and temperature sensors, and a guidewire.

The exemplary catheter 136 also includes a handle 156. The wound stylet pairs 148 and 150 pass through handle apertures 158 and 160 and the proximal ends of the stylet pairs may be provided with grips 162 and 164. The exemplary hoop structure 140 may be driven from the expanded orientation illustrated in FIG. 12 to the collapsed orientation illustrated in FIG. 14 by moving the stylet pair 148 (and stylets 148a and 148b) in the distal direction and moving the stylet pair 150 (and stylets 150a and 150b) in the proximal direction. Alternatively, the handle may be provided with conventional bi-directional steering apparatus, such as the rotatable knob arrangement illustrated in U.S. Pat. No. 5,254,088 or the rotatable gear and rack arrangement illustrated in U.S. Pat. No. 5,364,351, to drive the stylet pairs 148 and 150 in opposite directions. In any event, the handle 156 preferably also includes an electrical connector 166.

The exemplary catheter 136 may be advanced over a guidewire that passes through a lumen in the catheter body member 138. A relatively short introducer sheath or a sheath which extends to the anatomical region of interest may be used if desired. Here too, the hoop structure 140 can then be expanded and used to create an annular lesion without occluding blood flow.

The exemplary catheter illustrated in FIGS. 12–14 may also be used in conjunction with a mapping basket. As illustrated for example in FIG. 14a, a basket catheter 124 such as that illustrated in FIG. 11 may be advanced through the guidewire lumen of catheter 136. Alternatively, as illustrated for example in FIG. 14b, a modified catheter 136' includes a basket 128' mounted on the distal end of the catheter body 138.

Other types of lesion creating catheters may be provided with an integral mapping basket. As illustrated for example in FIG. 15, exemplary catheter 168 includes a proximal portion 170, a helical distal portion 172 and an integral mapping/coagulation basket 174. The helical distal portion 172 preferably supports a plurality of electrodes 176. The number of revolutions, length, diameter and shape of the helical portion 172 will vary from application to application. The helical portion illustrated in FIG. 15, which may be used to create lesions in or around the pulmonary vein, revolves around the longitudinal axis of the catheter 168 one and one-half times in its relaxed state. The basket 174, which is essentially the same as those described above, includes four splines 178 and a pair of electrodes 180 on each spline. Other basket configurations may be used as applications so require.

The exemplary catheter 168 also includes a stylet 182 that enables the physician to manipulate the helical distal portion 172 and adjust its shape. The distal portion of the stylet 182 is fixedly secured within the region of the catheter distal of the helical distal portion 172. The stylet 182 can be moved distally and proximally and can also be rotated in one direction, which will cause the helical portion of unwind so that its diameter decreases, or rotated in the other direction to cause its diameter to decrease. In any of these states, the helical portion will define an open area interior to the electrodes 176 through which blood or other bodily fluids can flow. As a result, the helical portion can be used to create a circumferential lesion in or around the pulmonary vein, or other bodily orifice, without occluding fluid flow.

Figure 15:
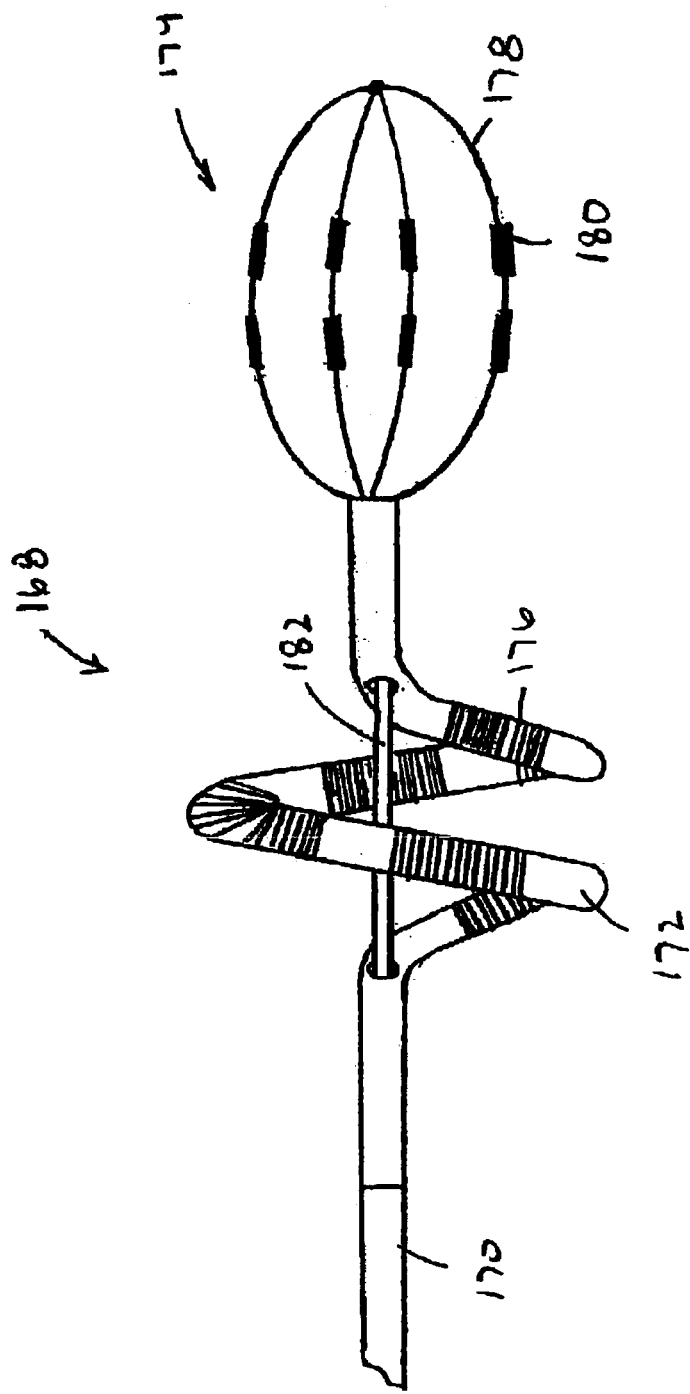
FIG. 15 is a side view of a probe in accordance with a preferred embodiment of a present invention.

The exemplary catheter 168 illustrated in FIG. 15 is not a steerable catheter and, accordingly, may be advanced though a conventional steerable guide sheath to the target location. The sheath should be lubricious to reduce friction during movement of the catheter 168. Prior to advancing the catheter 168 into the sheath, the stylet 182 will be moved to and held in its distal most position in order to straighten out the helical distal portion 172. The stylet 182 will remain in this position until the helical distal portion 172 is advanced beyond the distal end of the sheath. A sheath introducer, such as those used in combination with basket catheters, may be used when introducing the catheter into the sheath.

Additional information concerning the helical catheter illustrated in FIG. 15, albeit without the mapping basket, is disclosed in concurrently filed and commonly assigned U.S. application Ser. No. 09/447,186, which is entitled "Loop Structures For Supporting Diagnostic and Therapeutic Elements in Contact With Body Tissue" and incorporated herein by reference.

Another exemplary catheter with a hoop structure is illustrated in FIGS. 16–18. Referring first to FIG. 16, the catheter 184 includes a catheter body 186 and a collapsible hoop structure 188 at the distal end thereof. The hoop structure 188 may be used to support one or more operative elements, such as the illustrated electrodes 190, in contact with an annular tissue region such as the pulmonary vein. The exemplary hoop structure 188 includes a substantially circular hoop spline 192 and four support splines 194. The hoop spline 192 may also be oval, elliptical or any other shape, and the number of support splines 194 may be increased or decreased, as applications require. In an implementation suitable for pulmonary vein applications, the hoop spline 192 will be about 10 mm to about 30 mm in diameter.

As illustrated for example in FIGS. 17 and 18, the exemplary hoop structure 188 is composed of four substantially identical structural members 196, each of which consists of a pair of struts 198 and a curved portion 200 that extends approximately ninety degrees, and four molded tubes 202 that extend outwardly from the catheter body 186. One strut 198 from each of two adjacent structural members 196 is inserted into a tube 202. To that end, the struts 198 are formed with bends 204 so that the struts will conform to the shape of the region 206 that includes the distal portion of the catheter body 186 and the tubes 202 that extend outwardly therefrom. Each support spline 194 is, therefore, a composite structure consisting of two struts 198 and a molded tube 202. Wiring from the electrodes 190 and temperature sensors associated with the electrodes (not shown) will pass through the tubes 202 and into a lumen extending through the catheter body 186.

The structural members 196 are preferably formed from a resilient, biologically inert material such as Nitinol® metal, stainless steel or silicone rubber that is preshaped into the configuration corresponding to an expanded hoop structure 188. The catheter body 186 and molded tubes 202 may be formed from a biocompatible thermoplastic material such as braided or unbraided Pebax®, polyethylene, or polyurethane.

A relatively short introducer sheath and, preferably, a sheath which extends to the anatomical region of interest will be used in conjunction with the exemplary catheter illustrated in FIGS. 16–18. Here too, the hoop structure can be expanded and used to create an annular lesion at the entrance to or within, for example, the pulmonary vein without occluding blood flow.

As illustrated for example in FIG. 19, the exemplary hoop structure 188 illustrated in FIGS. 16–18 can be reconfigured slightly in order to increase the collapsibility of the structure. The exemplary hoop structure 188' is essentially identical to hoop structure 188 but for the configuration of the structural members 196. Here, the curved portions 200' in hoop structure 188' are rotated distally in the direction of the arrows "A" relative to the curved portions 200 in hoop structure 188 to increase the collapsibility.

Still another exemplary hoop structure is illustrated in FIG. 20 and generally represented by reference numeral 208. Here, the catheter is provided with a catheter body 210 and a collapsible hoop structure 212 at the distal end thereof. The hoop structure 212 may be used to support one or more operative elements, such as the illustrated electrodes 214, in contact with an annular tissue region such as the pulmonary vein. The exemplary hoop structure 212 includes a substantially circular hoop spline 216, four proximal support splines 218, four distal support splines 220, a base 222 and an end cap 224. In addition to providing additional structural support, the distal support splines 220 act as an anchor during tissue coagulation procedures. The hoop spline 214 will be about 10 mm to about 30 mm in diameter in implementations suitable for pulmonary vein applications. The hoop spline 216 may also be oval, elliptical or any other shape, and the number of support splines 218, 220 may be increased or decreased, as applications require.

IV. Hoop Structure Electrodes, Temperature Sensing and Power Control

In each of the preferred embodiments, the operative elements are a plurality of spaced electrodes. However, other operative elements, such as lumens for chemical ablation, laser arrays, ultrasonic transducers, microwave electrodes, and resistive heating wires, and such devices may be substituted for the electrodes. Additionally, although electrodes and temperature sensors are discussed below in the context of the exemplary catheter described with reference to FIGS. 7–11, the discussion is also applicable to the exemplary catheters described with reference to FIGS. 12–20.

The spaced electrodes 82 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 82 are electrically coupled to individual wires (such as those illustrated in FIG. 2) to conduct coagulating energy to them. The wires are passed in conventional fashion through a lumen extending through the associated catheter body into a PC board in the catheter handle, where they are electrically coupled to a connector that is received in a port on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 82 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

As illustrated for example in FIG. 9, a plurality of temperature sensors 83, such as thermocouples or thermistors, may be located on, under, abutting the longitudinal end edges of, or in between, the electrodes 82. Preferably, the temperature sensors 83 are located at the longitudinal edges of the electrodes 82 on the distally facing side of the hoop or helical structure. In some embodiments, a reference thermocouple (not shown) may also be provided. For temperature control purposes, signals from the temperature sensors are transmitted to the source of coagulation energy by way of wires (such as those illustrated in FIG. 2) that are also connected to the aforementioned PC board in the catheter handle. Suitable temperature sensors and controllers which control power to electrodes based on a sensed temperature are disclosed in U.S. Pat. Nos. 5,456,682, 5,582,609 and 5,755,715.

Finally, the electrodes 82 and temperature sensors 83 can include a porous material coating, which transmits coagulation energy through an electrified ionic medium. For example, as disclosed in U.S. application Ser. No. 08/879,343, filed Jun. 20, 1997, entitled "Surface Coatings For Catheters, Direct Contacting Diagnostic and Therapeutic Devices," electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A mapping and coagulation apparatus, comprising:
a tissue coagulation probe including
a tissue coagulation probe support body defining at least one interior lumen, and
an inflatable tissue coagulation structure supported on the tissue coagulation probe support body; and
a mapping probe passable through the tissue coagulation probe support body lumen including
a mapping probe support body, and
an expandable/collapsible mapping basket supported on the mapping probe support body.

2. A mapping and coagulation apparatus as claimed in claim 1, wherein the tissue coagulation probe support body comprises a catheter.

3. A mapping and coagulation apparatus as claimed in claim 1, wherein the inflatable tissue coagulation structure defines an interior and the tissue coagulation probe support body includes a fluid lumen operably connected to the interior of the inflatable tissue coagulation structure.

4. A mapping and coagulation apparatus as claimed in claim 1, wherein the inflatable tissue coagulation structure comprises a non-porous, relatively thermally conductive structure.

5. A mapping and coagulation apparatus as claimed in claim 4, further comprising:
a fluid heating element located within the interior of the inflatable tissue coagulation structure.

6. A mapping and coagulation apparatus as claimed in claim 1, wherein the inflatable tissue coagulation structure comprises a porous structure.

7. A mapping and coagulation apparatus as claimed in claim 6, wherein the porous structure includes a porous region and a non-porous region.

8. A mapping and coagulation apparatus as claimed in claim 6, further comprising:
an electrode located within the interior of the inflatable tissue coagulation structure.

9. A mapping and coagulation apparatus as claimed in claim 1, wherein the expandable/collapsible mapping basket comprises at least two splines respectively supporting at least two electrodes.

10. A mapping and coagulation apparatus, comprising:
a tissue coagulation probe including
a tissue coagulation probe support body defining at least one interior lumen and a distal end, and
an expandable/collapsible tissue coagulation structure supported on the tissue coagulation probe support body at least 3 cm from the distal end of the tissue coagulation probe support body; and
a mapping probe passable through the tissue coagulation probe support body lumen including
a mapping probe support body, and
a mapping structure supported on the mapping probe support body.

11. A mapping and coagulation apparatus as claimed in claim 10, wherein the tissue coagulation probe support body comprises a catheter.

12. A mapping and coagulation apparatus as claimed in claim 10, wherein the expandable/collapsible tissue coagulation structure comprises an inflatable structure.

13. A mapping and coagulation apparatus as claimed in claim 12, wherein the inflatable structure defines an interior and the tissue coagulation probe support body includes a fluid lumen operably connected to the interior of the inflatable structure.

14. A mapping and coagulation apparatus as claimed in claim 12, wherein the inflatable structure comprises a non-porous, relatively thermally conductive structure.

15. A mapping and coagulation apparatus as claimed in claim 14, further comprising:
a fluid heating element located within the interior of the inflatable structure.

16. A mapping and coagulation apparatus as claimed in claim 12, wherein the inflatable structure comprises a porous structure.

17. A mapping and coagulation apparatus, comprising:
a tissue coagulation probe including
a tissue coagulation probe support body defining at least one interior lumen and a distal end, and
an expandable/collapsible tissue coagulation structure supported on the tissue coagulation probe support body proximal to the distal end;
a mapping probe passable through the tissue coagulation probe support body lumen including a mapping probe support body, and a mapping structure supported on the mapping probe support body;

a thermocouple associated with the expandable/collapsible tissue coagulation structure; and a reference thermocouple supported on the tissue coagulation probe support body distal of the expandable/collapsible tissue coagulation structure.

18. A mapping and coagulation apparatus as claimed in claim 17, wherein the tissue coagulation probe support body comprises a catheter.

19. A mapping and coagulation apparatus as claimed in claim 17, wherein the expandable/collapsible tissue coagulation structure comprises an inflatable structure.

20. A mapping and coagulation apparatus as claimed in claim 19, wherein the inflatable structure defines an interior and the tissue coagulation probe support body includes a fluid lumen operably connected to the interior of the inflatable structure.

21. A mapping and coagulation apparatus as claimed in claim 19, wherein the inflatable structure comprises a non-porous, relatively thermally conductive structure.

22. A mapping and coagulation apparatus as claimed in claim 21, further comprising:

a fluid heating element located within the interior of the inflatable structure.

23. A mapping and coagulation apparatus as claimed in claim 19, wherein the inflatable structure comprises a porous structure.

* * * * *